United States Patent [19]

Arnaud et al.

[11] Patent Number: 5,750,095
[45] Date of Patent: *May 12, 1998

[54] ANHYDROUS COSMETIC OR DERMATOLOGICAL COMPOSITION CONTAINING THE COMBINATION OF A SILICONE OIL AND A WAX MADE FROM AN ETHYLENE HOMOPOLYMER OR COPOLYMER

[75] Inventors: Pascal Arnaud, Creteil; Myriam Mellul, L'Hay Les Roses, both of France

[73] Assignee: L'Oreal, Paris, France

[*] Notice: The term of this patent shall not extend beyond the expiration date of Pat. No. 5,556,613.

[21] Appl. No.: 672,082

[22] Filed: Jun. 26, 1996

Related U.S. Application Data

[63] Continuation of Ser. No. 377,382, Jan. 25, 1995, Pat. No. 5,556,613.

[30] Foreign Application Priority Data

Jan. 26, 1994 [FR] France .................. 94 00843

[51] Int. Cl.$^6$ .................. A61K 7/02; A61K 7/027
[52] U.S. Cl. .................. 424/64; 424/59; 514/844; 514/845
[58] Field of Search .................. 424/59, 63, 64; 252/16; 514/844, 845

[56] References Cited

U.S. PATENT DOCUMENTS

| | | | |
|---|---|---|---|
| 2,992,201 | 7/1961 | Gober | 260/29.1 |
| 4,200,561 | 4/1980 | Chang | 260/23 H |
| 5,143,723 | 9/1992 | Calvo et al. | 424/63 |

FOREIGN PATENT DOCUMENTS

| | | |
|---|---|---|
| 0205961 | 12/1986 | European Pat. Off. |
| 0385312 | 9/1990 | European Pat. Off. |
| 0511092 | 10/1992 | European Pat. Off. |

Primary Examiner—C. Warren Ivy
Assistant Examiner—Evelyn Huang
Attorney, Agent, or Firm—Nixon & Vanderhye PC

[57] ABSTRACT

A silicone oil-based anhydrous cosmetic or dermatological anhydrous composition having a homogeneous fatty phase wherein said fatty phase contains a silicone oil having the formula

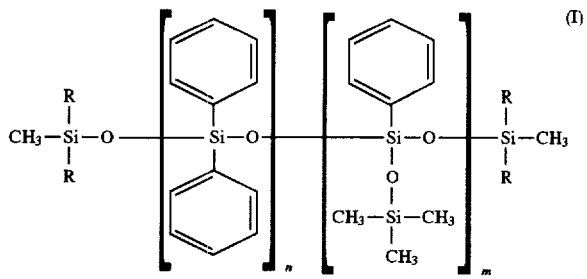

wherein R represents alkyl having 1 to 30 carbon atoms, aryl or aralkyl, n represents a whole number between 0 and 100, and m represents a whole number between 0 and 100, provided that the sum of n+m is between 1 and 100; and (ii) a wax in an amount ranging from 3 to 50 percent by weight based on the total weight of said fatty phase having a melting point between 50° and 135° C., comprising at least polymer having a molecular weight between 200 and 1,500 and selected from ethylene homopolymers and copolymers, and a monomer having the formula:

$$CH_2=CH-R' \quad (II)$$

wherein

R' represents alkyl having 1 to 30 carbon atoms, aryl or aralkyl.

10 Claims, No Drawings

ANHYDROUS COSMETIC OR DERMATOLOGICAL COMPOSITION CONTAINING THE COMBINATION OF A SILICONE OIL AND A WAX MADE FROM AN ETHYLENE HOMOPOLYMER OR COPOLYMER

This is a continuation of application Ser. No. 08/377,382, filed Jan. 25, 1995, now U.S. Pat. No. 5,556,613.

The present invention concerns an anhydrous cosmetic or dermatological composition containing, in its fatty phase, the combination of a silicone oil and a wax made from an ethylene homopolymer or copolymer.

The use of silicone oils to formulate products intended for topical application is especially desired, since these oils are harmless and, at the same time, possess a chemical inertia and highly satisfactory lubricating and film-forming properties. In particular, when applied on the skin or keratinic fibers, they produce a film exhibiting simultaneously a homogeneity, a softness, and a gloss that are especially satisfying.

The anhydrous compositions intended for topical application are normally solid or viscous compositions which require, for said application, the presence of waxes, such as natural or paraffin waxes.

However, when the proportions of silicone oil and wax exceed 5% and 3% by weight respectively, poor compatibility has been revealed, with the result that it is possible to obtain a homogeneous mixture after cooling only within markedly limited, predetermined proportion ranges. The term "homogeneous mixture" signifies a mixture in which the various constituents are distributed in identical fashion at all points within the mixture. The lack of constituent compatibility in a given mixture leads to the deterioration thereof, in particular because of the emergence of syneresis. It has been found, moreover, that the problem of compatibility linked to silicone oils arose with respect to the majority of waxes.

Various solutions have been considered to solve this problem. Accordingly, GB 1,140,536 describes waxes containing at least 15% silicone wax. In addition, EP-A-205,961 discloses the use of microcrystalline or hydrocarbon-containing paraffin waxes combined with a resin and a polyolefin. Furthermore, U.S. Pat. No. 5,085,855 describes the use of a combination of a lanolin oil, a lanolin wax, gelling agents, and hydrocarbon-containing polymers. However, according to these diverse solutions, the different constituents must be combined in limited, predetermined proportions, and any addition of a supplementary compound requires the prior preparation of a compatibility diagram which grows increasingly complex as the number of compounds in the composition increases.

After a great amount of research it has now been found, surprisingly and unexpectedly, that, by combining a particular silicone oil and a wax made from an ethylene homopolymer or copolymer, the choice of which was based both on the melting point and on the molecular mass, it was possible to produce silicone oil-based, homogeneous anhydrous cosmetic compositions, without being limited by a restrictive range of proportions.

Therefore, the present invention concerns a silicone oil-based anhydrous cosmetic or dermatological composition having a homogenous fatty phase, characterized by the fact that this fatty phase incorporates a mixture comprising:

(i) at least one silicone oil in a proportion of 5 to 97% by weight of said fatty phase and corresponding to the following formula:

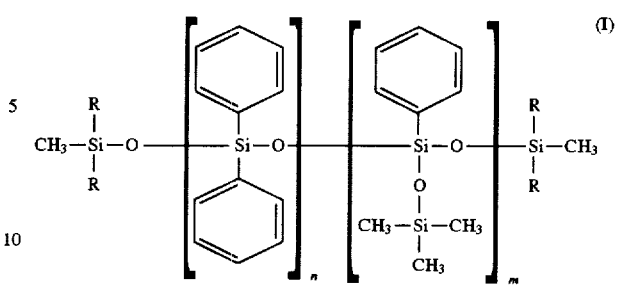

wherein

R represents alkyl containing 1 to 30 carbon atoms, aryl or aralkyl, n represents a whole number between 0 and 100, and m represents a whole number between 0 and 100, provided that the sum n+m is between 1 and 100; and (ii) a wax in a proportion of 3 to 50% of the total weight of said fatty phase, whose melting point is between 50° and 135° C. and which consists of at least one polymer having a molecular weight between 200 and 1,500 selected from ethylene homopolymers and copolymers, and a monomer corresponding to the formula:

$$CH_2=CH-R' \qquad (II)$$

wherein

R' represents alkyl having 1 to 30 carbons, aryl or aralkyl.

Alkyl having 1 to 30 carbons include methyl, ethyl, propyl, isopropyl, decyl, dodecyl, and octadecyl.

Aryl is, preferably, phenyl or tolyl.

The aralkyl is, preferably, benzyl or phenethyl.

Among the silicone oils of formula (I), use is preferably made of those having a viscosity, measured at 25° C., of between 5 and 500 centistokes (cSt).

Among the latter, mention may be made, in particular, of oil commercialized under the trade name "Abil AV 8853" by Goldschmidt, those commercialized under the trade names "DC 556" and "SF 558" by Dow Corning, and that commercialized under the trade name "Silbione 70633 V 30" by Rhone-Poulenc.

According to a preferred embodiment of the compositions according to the invention, the silicone oil of formula (I) is present in an amount between 10 and 90% by weight of the total weight of the fatty phase.

The use of waxes made from ethylene homopolymers or copolymers, such as those specified above, gives the mixture very numerous advantages. In effect, the mixture produced possesses a high degree of thermal stability, a thixotropy nature yielding excellent spreading properties, a very high degree of water-resistance imparting good cosmetic staying power to products applied to the skin and keratinic fibers. Moreover, these properties make it possible to spread a large quantity of solid particles while preserving good properties of application. In addition, since these products are synthesized, they do not exhibit the variability problems found with natural compounds.

According to a preferred embodiment of the compositions according to the invention, the wax used as previously specified is chosen from among ethylene homopolymers, ethylene-propylene copolymers, and ethylene-hexene copolymers.

The ethylene homopolymers useful according to the invention include, in particular, those sold under the trade names "Polywax 500", "Polywax 655", and "Polywax 1.000" by Bareco, those sold under the trade names "PE 1.500 F" and PEW 1.555" by Langer & Co., those commercialized under the trade name "TN Wax 1.495" sold by R.T. Newey, and "AC 1702" sold by Allied Chemical.

Ethylene polymers usable within the scope of the invention include the ethylene-propylene copolymers sold under the trade names "Petrolite CP-7" and "Petrolite CP-12" sold by Bareco, and the ethylene-hexene copolymers sold under the trade names "Petrolite CH-7" and "Petrolite CH-12" by Bareco.

According to a preferred embodiment of the compositions according to the invention, the wax used as described above is present in an amount between 5 and 30% by weight of the total weight of the fatty phase.

The mixture of a silicone oil and a wax made from an ethylene homopolymer or copolymer, as described above, is generally present in the composition according to the invention in a proportion of between 3 and 100% by weight of the total weight of the composition.

In addition to the two constituents of the mixture described above, the fatty phase can also incorporate additives or fatty substances selected from oils and/or waxes. The proportion of additive or fatty substance present in the composition according to the invention is generally between 0.5 and 92% by weight of the total weight of the fatty phase, and preferably between 2 and 85%.

Contrary to known compositions, for which complex compatibility diagrams must be prepared, i.e., diagrams accounting for all of the components of the composition, it suffices merely to prepare, for the compositions according to the invention, a compatibility diagram for the additive in conjunction with one of the compounds in the combination, that is, with the ethylene homopolymer or copolymer wax or with the silicone oil. If the additive is compatible with one of these two components, it is necessarily compatible with the combination thereof.

The oils eventually present in the fatty phase can be of mineral, animal, vegetable, or synthetic origin.

Oils of mineral origin include paraffin oil and vaseline oil. Mineral oils, in general, have a boiling point between 310° and 410° C.

As an animal oil, perhydrosqualene can be cited.

Vegetable oils include, in particular, sweet almond oil, calophyllum oil, palm oil, avocado oil, jojoba oil, sesame oil, olive oil, castor oil and cereal germ oils, e.g., wheat germ oil.

Among the synthetic oils, mention may be made of synthetic esters such as Purcellin oil, butyl myristate, isopropyl myristate, cetyl myristate, isopropyl palmitate, butyl stearate, hexadecyl stearate, isopropyl stearate, octyl stearate, isocetyl stearate, decyl oleate, hexyl laurate, propylene glycol dicaprylate and diisopropyl adipate.

Other oils useful in the compositions according to the invention include organic alcohols, such as oleic alcohol, linoleic alcohol, linolenic alcohol, isostearyl alcohol and octyldodecanol, and esters derived from lanolic acid, such as isopropyl lanolate and isocetyl lanolate.

Mention may also be made of acetylglycerides, octanoates, and decanoates of alcohols and polyhydric alcohols, such as those of glycol and glycerol, as well as the ricinoleates of alcohols and polyhydric alcohols, such as those of cetyl.

The waxes potentially present in the fatty phase may be of mineral, fossil, animal, or vegetable origin, or they may be hydrogenated oils or fatty esters solid at 25° C.

The mineral waxes useful according to the invention include microcrystalline, paraffin, vaseline and ceresin waxes.

Fossil waxes include ozokerite and montana wax.

Among animal waxes, mention can be made of beeswax, spermaceti, lanolin wax, and derivatives of lanolin, such as lanolin alcohols, hydrogenated lanolin, hydroxylated lanolin, acetylated lanolin, fatty lanolin acids and acetylated lanolin alcohol.

Vegetable waxes include candellila wax, carnauba wax, Japan wax and cocoa butter.

Hydrogenated oils solidified at 25° C. include hydrogenated ricin oil, hydrogenated palm oil, hydrogenated tallow and hydrogenated coconut oil.

Fatty esters solidified at 25° C. include propylene glycol monomyristate and myristyl myristate.

In addition, the group of waxes comprises cetyl alcohol, stearyl alcohol, mono-, di-, and triglycerides solidified at 25° C., stearic monoethanolamide, colophane and the derivatives thereof, such as glycol and glycerol abietates, sucroglycerides, and calcium, magnesium, zinc, and aluminum oleates, myristates, lanolates, stearates and dihydroxystearates.

The proportion of wax, as specified above, is preferably less than or equal to the proportion of ethylene homopolymers or copolymers.

Furthermore, in the fatty phase of compositions according to the invention oily gel agents can be employed.

These oily gel agents include, in particular, metallic esters, such as polyoxyaluminum stearate and aluminum or magnesium hydroxystearate, cholesterol derivatives and, in particular, hydroxycholesterol, and argillaceous minerals which swell in the presence of oil, and, in particular, those belonging to the montmorillonite group.

According to a special embodiment, the compositions according to the invention may further contain charges, that is, solid compounds in powder form. The proportion of charges in the compositions according to the invention generally ranges between 0.5 and 97% by weight, and preferably between 1 and 40% by weight of the total weight of the composition.

The powdered compounds useful according to the invention may be natural or synthetic, and include, in particular:

a) mineral powders, such as talcum, kaolin, mica, silica, silicates, alumina, zeolites, hydroxyapatite, sericite, titanium dioxide, micatitaniums, zinc oxide, barium sulfate, iron oxides, manganese purple, chrome oxide, cobalt blue, bismuth oxychloride, boron nitride, and metallic powders such as powdered aluminum;

b) vegetable powders, such as cornstarch, wheat, or rice powder;

c) organic powders, such as nylon, polyamide, polyester, polytetrafluoroethylene, or polyethylene powders; and d) organo-metallic powders, such as pigments including zirconium, barium, or aluminum with organic coloring agents.

The powders described above can also be coated, for example using metallic salts of fatty acids, amino acids, lecithin, collagen, silicone-containing compounds, fluorinated compounds, fluorosilicone-containing compounds, or any other conventional coating.

The compositions according to the invention can further comprise a lipophilic additive chosen from among surface active agents, filters, vitamins, hormones, antioxidants, preservatives, dyes, perfumes, and mixtures thereof.

The cosmetic or dermatological compositions according to the invention can exist in various forms, such as oily gels, solid products such as compressed powders or sticks. They can be used, in particular, as skin-care, cleansing or makeup products.

In the case of makeups, these compositions can exist, in particular, as foundations, mascaras, lipsticks, eyeliners or blushers.

The compositions according to the invention are prepared according to conventional methods; that is, by homogenization under heat, then cooling, of the various constituents thereof.

The various composition forms, described above, are obtained based on the nature and proportions of the compounds added thereto, and on the cooling method employed. Thus, by simple cooling with or without stirring, a gel incorporating the composition can be produced. Compositions produced in different forms can also be obtained by pouring the heated mixture in different types of packaging.

Products in compressed form are obviously obtained by exerting pressure on the product.

Illustrative examples of compositions according to the present invention are now given as illustrations.

EXAMPLE 1

Oily Gel

| Phase A: | |
|---|---|
| Silicone oil sold under the trade name "SF-558" by Dow Corning | 55 g |
| Sesame oil | 20 g |
| Phase B: | |
| Ethylene homopolymer sold under the trade name "AC 1702" by Allied Chemical Company | 20 g |
| Ethylene homopolymer sold under the trade name "Polywax 655" by Bareco | 5 g |

Phase A was prepared by mixing the constituents thereof while stirring at ambient temperature. After homogenization, the constituents of phase B were added, then the mixture was heated to about 107° C. After melting and homogenization, a clear medium was obtained. The oily gel is then obtained by cooling to ambient temperature.

The gel thus obtained presented excellent spreading properties and formed a very soft and protective film.

EXAMPLE 2

Makeup Foundation

| Phase A: | |
|---|---|
| Silicone oil sold under the trade name "DC-556" by Dow Corning | 14 g |
| Hollow microspheres made of a thermoplastic material sold under the trade name "Expancel 551 DE" by Casco-Nobel | 1.5 g |
| Phase B: | |
| Ethylene homopolymer sold under the trade name "PEW 1555" by Langer | 7 g |
| Microcrystalline wax | 4 g |
| Phase C: | |
| 2-hexyl ethyl palmitate | 19 g |
| Hydrogenated isoparaffin | 14 g |
| Isopropyl lanolate | 9.3 g |
| Propyl paraben | 0.2 g |

| -continued | |
|---|---|
| Phase D: | |
| Iron oxides | 3 g |
| Titanium dioxide | 13 g |
| Zinc oxide | 3 g |
| Talcum | 12 g |

The constituents of phases B and C were mixed, then heated to approximately 107° C. After melting all of the constituents, the mixture was homogenized, then cooled to a temperature of approximately 90° C. Phase A, whose constituents have been preliminarily mixed at ambient temperature, and, finally, the constituents of phase D were added in succession. After homogenization, the mixture thus obtained was poured under heat into cupels.

After cooling at ambient temperature, a makeup foundation was obtained which possessed excellent skin-spreading properties and very good staying power.

EXAMPLE 3

Lipstick

| Phase A: | |
|---|---|
| Silicone oil sold under the trade name "DC-556" by Dow Corning | 23 g |
| Phase B: | |
| Ethylene homopolymer sold under the trade name "PEW 1555" by Langer | 7 g |
| Microcrystalline wax | 7 g |
| Lanolin | 7 g |
| Phase C: | |
| Ricin oil | 22 g |
| Sesame oil | 22 g |
| Phase D: | |
| Pigments | 12 g |

The constituents of phases B and C were mixed by heating at approximately 107° C. After the waxes were melted, the mixture was homogenized, then cooled to approximately 95° C. Phase A, then phase D were added in succession. After homogenizing the mixture, the latter was poured into stick-shaped compartments.

After cooling, a lipstick was obtained which was applied quite easily to the lips and had a very high degree of softness. Moreover, it stayed in place well; that is, it showed excellent resistance and did not run.

EXAMPLE 4

Lipstick

| Phase A: | |
|---|---|
| Silicone oil sold under the trade name "Silbione 70633 V 30" by Rhone-Poulenc | 10 g |
| Jojoba oil | 25 g |
| Sesame oil | 27 g |
| Phase B: | |
| Ethylene homopolymer sold under the trade name "Polywax 500" by | 20 g |

-continued

| | |
|---|---|
| Bareco Lanolin | 6.5 g |
| Phase C: | |
| Pigments | 11.5 g |

EXAMPLE 5

Lipstick

| Phase A: | |
|---|---|
| Silicone oil sold under the trade name "Silbione 70633 V 30" by Rhone-Poulenc | 10 g |
| Jojoba oil | 25 g |
| Sesame oil | 27 g |
| Phase B: | |
| Ethylene copolymer and propylene sold under the trade name "Petrolite CP-7" by Bareco | 20 g |
| Lanolin | 6.5 g |
| Phase C: | |
| Pigments | 11.5 g |

The lipsticks in Examples 4 and 5 are prepared in a manner similar to that of Example 3.

We claim:

1. An anhydrous silicone oil-based make-up composition containing:

(a) a homogeneous fatty phase, said fatty phase comprising a mixture of:
   (i) 5 to 90% by weight of said fatty phase of at least one silicone oil having the formula:

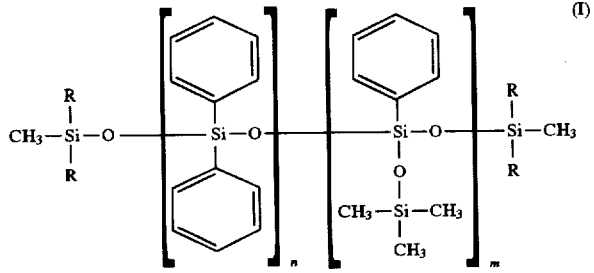

(I)

wherein;

R represents alkyl having 1 to 30 carbon atoms, aryl or aralkyl, n represents a whole number between 0 and 100, and m represents a whole number between 0 and 100, provided that the sum of n+m is between 1 and 100;

(ii) 3 to 50% by weight of said fatty phase of an ethylene homopolymer wax having a melting point between 50° C. nd 135° C. and a molecular weight between 200 and 1,500, and (iii) 0.5 to 85% by weight of said fatty phase of a fatty substance selected from the group consisting of an oil, a wax and a mixture thereof, and (b) 0.5 to 97% by weight of said anhydrous make-up composition of a solid compound in powder form.

2. The composition of claim 1, wherein in said silicone oil of formula (I) n=0 and R represents methyl.

3. The composition of claim 1, wherein said silicone oil has a viscosity of between 5 and 100 cst.

4. The composition of claim 1, wherein said silicone oil is present in an amount of 10 to 90% by weight based on the total of said fatty phase.

5. The composition of claim 1, wherein said ethylene homopolymer wax is present in an amount of 5 to 30% by weight based on the total of said fatty phase.

6. The composition of claim 1, wherein said solid compound in powder form is present in an amount of 1 to 40% by weight of said anhydrous make-up composition.

7. The composition of claim 1, wherein said solid compound in powder form is at least one pigment.

8. The composition for claim 1, wherein said fatty phase further contains an oily gel agent.

9. The composition of claim 1, which further contains a cosmetically acceptable lipophilic additive selected from the group consisting of a surface active agent, a filter, a vitamin, a hormone, an antioxidant, a preservative, a dye, a perfume and a mixture thereof.

10. The composition of claim 1, which is in the form of a lipstick or a make-up foundation.

* * * * *